(12) United States Patent
Gonzalez et al.

(10) Patent No.: US 7,850,696 B2
(45) Date of Patent: Dec. 14, 2010

(54) DEVICE FOR FACILITATING REDUCTION AND REPAIR OF FRACTURES OF THE SMALL BONES

(75) Inventors: Mark H. Gonzalez, Chicago, IL (US); Jack F. Long, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 1069 days.

(21) Appl. No.: 11/237,009

(22) Filed: Sep. 28, 2005

(65) Prior Publication Data

US 2007/0083211 A1 Apr. 12, 2007

(51) Int. Cl.
*A61B 17/56* (2006.01)

(52) U.S. Cl. ................................... 606/86 R

(58) Field of Classification Search .............. 606/96, 606/54, 281, 104
See application file for complete search history.

(56) References Cited

U.S. PATENT DOCUMENTS

| 4,262,386 A | 4/1981 | Saget |
| 4,312,337 A | 1/1982 | Donohue |
| 4,796,612 A | 1/1989 | Reese |
| 5,014,970 A | 5/1991 | Osipov |
| 5,320,622 A | 6/1994 | Faccioli et al. |
| 5,458,602 A * | 10/1995 | Goble et al. ............... 606/96 |
| 5,630,815 A | 5/1997 | Pohl et al. |
| 5,649,931 A * | 7/1997 | Bryant et al. ............. 606/104 |
| 5,863,292 A | 1/1999 | Tosic |
| 5,928,230 A | 7/1999 | Tosic |
| 6,120,511 A * | 9/2000 | Chan ........................ 606/96 |
| 6,146,384 A | 11/2000 | Lee et al. |
| 2003/0225408 A1* | 12/2003 | Nichols et al. ............. 606/61 |
| 2004/0122437 A1* | 6/2004 | Dwyer et al. ............... 606/87 |

* cited by examiner

*Primary Examiner*—Todd E Manahan
*Assistant Examiner*—Elana B Fisher
(74) *Attorney, Agent, or Firm*—Maginot, Moore & Beck (57) ABSTRACT

An apparatus for reducing a fracture in a bone and attaching a plate to the bone includes a first sub-assembly configured to reduce the fracture, and a second sub-assembly integrated with said first sub-assembly in a single surgical instrument. The second sub-assembly is configured to hold the plate against the bone concurrently with reduction of the fracture by the first sub-assembly.

5 Claims, 5 Drawing Sheets

DEVICE FOR FACILITATING REDUCTION AND REPAIR OF FRACTURES OF THE SMALL BONES

BACKGROUND AND SUMMARY

This disclosure relates to a device for reducing and repairing fractures of small bones and more particularly to a device for reducing fractures of the bones of the hands and feet, for clamping plates to those bones and for guiding a drill during drilling of the plate and bone to facilitate attachment of the plate to the bone.

Typically, fractures of the bones of the hands (e.g., the metacarpals) and feet (e.g., the phalanges) are reduced and then a plate is secured to the bone with bone screws passing through the bone and the plate on opposite sides of the fracture to hold the bone sections in place during healing. It is often difficult for surgeons to reduce a fracture while simultaneously positioning and affixing a plate to the fractured bone. Currently, surgeons must hold a plate on the bone with either a clamp or their hands while screw holes are drilled through the plate and into the bone. These screw holes must be drilled in the precise location and orientation the surgeon desires. Since the bones of the hands and feet are relatively small, there is little margin of error to correct for misplaced screw holes.

Most surgeons use medical pliers or other small clamping devices to perform the aforementioned functions. However, these instruments are not designed to simultaneously reduce a fracture and secure a plate in a desired location. As a result, it is often difficult to correctly position the pliers or clamping devices and still allow enough room to drill holes and place screws. Additionally, in order to accurately drill screw holes, a second device is required. Currently a hand held drill guide or a clamp containing a point contract drill guide is used to guide the drill while drilling holes through the plate and into the bone. Thus, a minimum of two clamps are currently typically used to perform fracture reduction, clamping of a plate to the reduced bone and securing of a drill guide in a desired location to guide a drill while drilling through the plate and into the bone.

This invention serves as both an external plate to bone clamp and reduction device for use with fractures of the hands and feet. The proximal portion of the device contains a bone hook, which can be adapted to fit around different bone diameters. The distal section of the device contains a thumbscrew assembly, which moves the reduction device and plate fixation pin away from and towards the fracture. Additionally, the medial section of the device contains a removable dial-able drill guide and a single hand operation handle. This disclosure is for a plate to bone clamp which also serves as a reduction device and drill guide.

The thumbscrew assembly of this device allows the surgeon to quickly reduce a fracture and temporarily clamp a plate in the desired location for attachment to the bone while holes are drilled through the plate into the bone at the desired locations. A removable drill guide is provided that allows a surgeon to visualize the placement of the drill and precisely control the orientation of the drill during the drilling operation. Thus, the disclosed device advantageously saves operating room time and allows for more accurate and less cumbersome procedure for repair of fractures of small bones.

According to one aspect of the disclosure, a surgical instrument for repairing a fracture in a small bone comprises a body portion, a first and second bone-engaging member, and a plate fixation member. The body portion is configured to facilitate manipulation of the surgical instrument. The first bone-engaging member is coupled to the body and configured to engage a first side of the small bone having a fracture therein at a first location. The second bone-engaging member is coupled to the body and configured to engage upon movement relative to the first bone-engaging member the small bone having the fracture in a position relative to the first location to facilitate in cooperation with the first bone-engaging member reduction of the fracture in the small bone. The plate fixation member is coupled to the body for movement relative to the body from a first position in which a plate can be inserted between the plate fixation member and the small bone and a second position in which a plate inserted between the plate fixation member and the small bone is temporarily fixed to the small bone.

According to a second aspect of the disclosure, a method of repairing a fracture in a fractured small bone is disclosed. According to the method a single instrument configured to capture a fractured small bone between a first member and a second member configured to move longitudinally with respect to each other and configured to engage a plate and seat the plate against the fractured small bone upon longitudinal movement of a third member with respect to the second member is provided. The first member of the instrument is disposed on a first side of the fractured small bone. The second member is disposed on a different side of the small bone. The fracture in the small bone is reduced by moving the first member relative to the second member to capture the fractured small bone between the first and second members. A plate is placed in engagement with the fractured small bone. The plate is seated against the fractured small bone by moving the third member longitudinally relative to the second member to bring the third member into engagement with the plate.

The above-noted features and advantages of the present invention, as well as additional features and advantages, will be readily apparent to those skilled in the art upon reference to the following detailed description and the accompanying drawings, which include a disclosure of the best mode of making and using the invention presently contemplated.

BRIEF DESCRIPTION OF THE DRAWINGS

In describing the disclosed device, reference will be made to the following figures in which.

Corresponding reference characters indicate corresponding parts throughout the several views. Like reference characters tend to indicate like parts throughout the several views.

DETAILED DESCRIPTION

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Referring to FIGS. 1-4, there is shown a device for facilitating reduction and repair of fractures of small bones 10. The device or surgical instrument 10 includes a plate fixation pin 12, a thumbscrew assembly 14, a body 16, a hollow shaft 18, a handle 20, a hook assembly 22 and a bone-engaging assembly 24. The device 10 includes a distal section 26, a medial section 28 and a proximal section 30. A removable drill guide assembly 32 is configured to be removably coupled to the medial section 28 of the device 10.

The hollow shaft 18 includes an outside wall 34 and an inside wall 36 defining a lumen 38 all of which are formed concentrically about a longitudinal axis 40. The hollow shaft 18 extends longitudinally between the distal section 26 and the proximal section 30. Adjacent the distal end of the hollow shaft 18, the outside wall 34 is formed to include a screw thread 42 to facilitate attachment of the thumbscrew assembly 14 to the hollow shaft 18. The thumbscrew assembly 20 located in the distal section 12 of the device is coupled to the hollow shaft 18 to control vertical movement of the hollow shaft 18 along its longitudinal axis 40 relative to the body 16 of the device. Also adjacent the distal end of the hollow shaft 18, the inside wall 36 is formed to include a screw thread 44 to facilitate attachment of the plate fixation pin 12 to the hollow shaft 18 for longitudinal movement of the plate fixation pin 12 relative to the hollow shaft 18.

The body 16 includes a cylindrical outer wall 46 extending between two annular radially outwardly extending lips 48, 50, a handle 20 extending from the distal lip 50, an attachment flange 54 extending from the proximal lip 48 and a cylindrical inner wall 56 defining a shaft-receiving bore 58. A distal wall 60 of the proximal lip 48, a proximal wall 62 of the distal lip 50 and the cylindrical outer wall 46 define a guide-receiving channel 64 extending circumferentially about the body 16 which is configured to receive the drill guide assembly 32 for fixation in a plurality of radial orientations relative to the body 16 in a manner described more fully below.

The cylindrical inner wall 56, cylindrical outer wall 46 and lips 48, 50 are formed concentrically about a longitudinal axis 66 of the body 16. The shaft-receiving bore 58 has an inside diameter 68 slightly greater than, but approximately equal to, the outside diameter 70 of the hollow shaft 18. Thus, the shaft-receiving bore 58 is configured to receive the hollow shaft 18 therein for longitudinal movement of the hollow shaft 18 relative to the body 16. When received in the shaft-receiving bore 58, the longitudinal axis 40 of the hollow shaft 18 is coincident with the longitudinal axis 66 of the body 16. The thumb screw assembly 14 cooperates with the distal lip 50 and the external threads 42 on the outer wall 34 of the hollow shaft 18 to limit the longitudinal movement of the hollow shaft 18 relative to the body 16.

Illustratively, the handle 20 includes an outwardly extending attachment arm 72 and a downwardly extending grip 74. The attachment arm 72 is coupled at a first end 76 to the distal lip 50 of the body 16 and extends radially outwardly from the body 16. A second end 78 of the attachment arm 72 is coupled to a first end 80 of the grip 74. The grip 74 extends downwardly from the attachment arm 72 for a distance 82 sufficient to permit a surgeon to comfortably hold the grip 74. The attachment arm 72 extends outwardly from the body a distance 84 sufficient to permit a surgeon to comfortably grasp the grip 74 without interfering with the attachment flange 54. The illustrated attachment arm 72 initially curves upwardly as it extends radially away from the distal lip 50 and then adjacent the second end 78 curves downwardly. The second end 86 of the grip 74 may be curved, as shown, for example, in FIGS. 1-3 and is illustratively free from the remainder of the device 10. In the illustrated embodiment, the grip 74 includes a straight section 88 that is substantially parallel to the longitudinal axis 66 of the body 16. The curvature of the attachment arm 72 permits the straight section 88 of the grip 74 to be long enough to allow the surgeon to comfortably grip the instrument 10 while ensuring that the free end 86 of the grip 74 does not engage the tissue surrounding the surgical site. While described as separate components, the illustrated attachment arm 72 and grip 74 of the handle 52 are formed as monolithic unit.

The attachment flange 54 includes a radially extending offset arm 90 and a longitudinally extending attachment arm 92. The first end 94 of the offset arm 90 is coupled to the proximal lip 48 of the body 16 at a position below the attachment location of the handle 52. The offset arm 90 extends radially outwardly from the body 16 in the same radial direction as the attachment arm 72 of the handle 52. The second end 96 of the offset arm 90 is displaced from the first end 94 by length 98. Length 98 is selected to displace the attachment arm 92 a sufficient distance away from the hollow shaft 18 so as not to interfere with movement of the shaft 18 relative to the body 16, to not interfere with the bone-engaging assembly 24, to not interfere with the ability of the surgeon to grasp the handle 52 and to allow the hook assembly 22 to engage the opposite side of the bone from the side the bone-engaging assembly 24 engages.

The first end 100 of the attachment arm 92 is coupled to the second end 96 of the offset arm 92. The attachment arm 92 is substantially straight and extends downwardly substantially parallel to the longitudinal axis 66 of the body 16. The second or free end 102 of the attachment arm 92 is displaced from the first end 100 by a displacement 104. The displacement 104 is selected to allow the hook assembly 22 to slide longitudinally relative to the attachment arm 92 to facilitate adjustment of the hook assembly 22 based on the diameter of the bone being reduced and clamped. In the illustrated embodiment, the attachment arm 92 is formed symmetrically about a longitudinal axis 106 and has a cross-sectional shape conforming to a cross-sectional shape of a cavity 168 in an attachment housing 150 of the hook assembly 22. Illustratively, the attachment arm 92 has a rectangular cross-sectional shape as the cross-sectional shape of a cavity 168 in an attachment housing 150 of the hook assembly 22 is rectangular. The outside dimensions of the attachment arm 92 are sized to be slightly less than, but substantially equal to, the inside dimensions of the cavity 168 in the attachment housing 150 of the hook assembly 22.

The bone-engaging assembly 24 is attached to the proximal end of the hollow shaft 18. The bone-engaging assembly 24 includes attachment fasteners 108, a first frame member 110, a second frame member 112, a first foot 114, a second foot 116, a first fastener 118 and a second fastener 120. In the illustrated embodiment, the first and second frame members 110, 112 are bars that are attached at their centers on opposite sides of the outside wall 34 of the proximal end of the hollow shaft 18. Each frame member 110, 112 is illustratively attached to the hollow shaft 18 utilizing an attachment fastener 108 that extends into the outer wall 34 of the hollow shaft 18 but do not extend into the lumen 38 so as not to interfere with reciprocal longitudinal movement of the plate fixation pin 12 within the lumen 38 relative to the shaft 18.

The first frame member 110 is formed symmetrically about a longitudinal axis 122 and includes a first end 124 and a second end 126. The first frame member 110 is formed to include a first foot attachment hole 128 extending through the bar perpendicular to the longitudinal axis 122 at a location between the center and the first end 124. The first frame member 110 is also formed to include a second foot attachment hole 130 extending through the bar perpendicular to the longitudinal axis 122 at a location between the center and the second end 126. The second frame member 112 is formed symmetrically about a longitudinal axis 132 and includes a first end 134 and a second end 136. The second frame member 112 is formed to include a first foot attachment hole 138 extending through the bar perpendicular to the longitudinal axis 132 at a location between the center and the first end 134. The second frame member 112 is also formed to include a second foot attachment hole 140 extending through the bar perpendicular to the longitudinal axis 132 at a location between the center and the second end 136.

The first and second frame members 110, 112 are attached to the proximal end of the hollow shaft 118 so that their respective longitudinal axes 122, 132 are substantially perpendicular to the longitudinal axis 40 of the hollow shaft 18, substantially parallel to the radius along the direction in which both the attachment arm 72 of the handle 52 and the offset arm 90 of the attachment flange 54 extend away from the body 16, and substantially perpendicular to the attachment arm 92 of the attachment flange 54. When the first and second frame members 110, 112 are attached at their centers, the first attachment holes 128, 138 and the second attachment holes 130, 140 align. As a result of this alignment, the first fastener 118 can be inserted through the first attachment hole 128 of the first frame member 110 and the first attachment hole 138 of the second frame member 112 and an attachment hole 142 in the first foot 114 to secure the first foot 114 between both frame members 110, 112. Similarly, as a result of this alignment, the second fastener 120 can be inserted through the second attachment hole 130 of the first frame member 110 and the second attachment hole 140 of the second frame member 112 and an attachment hole 144 in the second foot 116 to secure the second foot 116 between both frame members 110, 112. When so attached the first and second feet 114, 116 are on opposite sides of the hollow shaft and the bone-engaging end 146 of the first foot 114 and the bone engaging-end 148 of the second foot 116 extend longitudinally beyond the proximal end of the hollow shaft 18.

The hook assembly 22 includes an attachment housing 150, a position locking screw 152 and a bone-engaging hook arm 156. The attachment housing 150 is includes a body 158 having an outer wall 160, an upper wall 162, a lower wall 164 and an inner wall 166. The inner wall 166 defines a cavity 168 extending longitudinally through the body 158 between the upper wall 162 and lower wall 164. A threaded screw hole 170 is formed through the body 158 and extends between the outer wall 160 and the inner wall 162. The threaded screw hole 170 is sized and threaded to receive and cooperate with the threaded shaft 172 of the position locking screw 152 to allow the screw 152 to be tightened in the screw hole 170 so that the end 174 of the shaft 172 engages the attachment arm 92 of the attachment flange 54 to lock the attachment housing 150 in a position relative to the attachment flange 54 when the head 176 of the locking screw 152 is turned. Since the attachment arm 92 in the illustrated embodiment has a rectangular cross-sectional shape the cavity 168 in the attachment housing 150 of the hook assembly 22 also has a rectangular cross-sectional shape. The outside dimensions of the attachment arm 92 are sized to be slightly less than, but substantially equal to, the inside dimensions of the cavity 168 in the attachment housing 150 of the hook assembly 22 to allow the attachment housing 150 to move longitudinally relative to the attachment arm 92 when the attachment arm 92 is received in the cavity 168. Illustratively, the attachment housing 150 is sized to be received between the frame members 110, 112 of the bone-engaging assembly 24.

The bone-engaging hook arm 156 includes a first end 178 and a second or free end 180. Illustratively, the bone-engaging hook arm 156 is fabricated from curved bar stock material having an inner surface 182 facing toward the hollow shaft 18 and an oppositely facing outer surface 184. Side walls 186 and 188 extend between and couple the inner and outer surfaces 182, 184. The first end 178 is coupled to the bottom wall 164 of the body 158 of the attachment housing 150. The hook arm 156 extends downwardly and curves inwardly toward the free end 180 to form a hook or cradle for engaging the opposite side of the bone from the bone-engaging feet of the assembly 22. In the illustrated embodiment, the inner surface 182 adjacent the free end 180 is displaced from the first end 178 by a displacement 190. The displacement 190 is selected based upon the size of bone within which a fracture is to be reduced. While only a single bone-engaging hook arm 22 is illustrated, it is envisioned that a plurality of bone engaging hook arms will be provided having different displacements 190 so that a surgeon can select the hook arm best suited for the size of the bone in which a fracture is to be reduced.

The plate fixation pin 12 includes a head 192 and a shaft 194 having an outer cylindrical wall 196 formed concentrically about a longitudinal axis 198, a first end 200 and a second, free or plate-engaging end 202. The first end 200 of the shaft 194 is coupled to the head 192 of the plate fixation pin 12. The outer cylindrical wall 196 has a diameter 204 that is approximately equal to but slightly less than the inside diameter of the lumen 38 of the hollow shaft 18. Thus when the shaft 194 of plate fixation pin 12 is received in the lumen 38 of the hollow shaft 18, the plate fixation pin 12 may reciprocate longitudinally along the longitudinal axis 198, which coincides with the longitudinal axis 40 of the hollow shaft 18, relative to the hollow shaft 18.

Adjacent the first end 200, the outer wall 196 is formed to include an external thread 206 configured to mate and cooperate with the internal thread 44 formed adjacent the distal end of the inside wall 36 of the hollow shaft 18. Thus by grasping the head 192 and rotating it in one direction or the other, the relative longitudinal position of the fixation pin 12 relative to the hollow shaft 18 can be controlled. The head 192 may be knurled to facilitate this rotation. The shaft 194 has a length 208 greater than the length 52 of the hollow shaft 18 by an amount sufficient to allow translation of the shaft 194 sufficiently to bring the free end 202 into contact with a plate 400 secured against the bone 402 to be repaired. The external thread 206 on the shaft 194 and the internal thread 44 are formed to allow the free end 202 of the shaft 194 to be moved relative to the proximal end of the hollow shaft 18 to clamp a plate 400 against a bone 402 held between the bone-engaging ends 146, 148 of the feet 114, 116 and the inner surface 182 of the bone-engaging hook arm 156.

The thumb screw assembly 14 is coupled to the top wall of the body 16 and is configured to control the relative position of the hollow shaft 18 relative to the body 16. The thumb screw assembly 14 includes a housing 210 and a thumb screw 212. The housing 210 includes an outer wall 214, a proximal end wall 216, a distal end wall 218, an inner cavity wall 220 and a longitudinal axis 222. The outer wall 214 and inner cavity wall 220 are formed concentrically about the longitudinal axis 222. The inner cavity wall 220 defines a shaft-receiving cavity 224 extending through the housing 210 between a proximal opening 226 in the proximal wall 216 and a distal opening 228 in the distal wall 218 of the housing 210. Illustratively, the shaft-receiving cavity 224 has an inside diameter 230 that is slightly larger than, but approximately equal to the outside diameter 35 of the hollow shaft 18. The shaft-receiving cavity 224 communicates with the shaft-receiving bore 58 formed in the body 16 so that the hollow shaft 18 can be received through the cavity 224 and bore 58 for longitudinal movement relative to the thumb screw assembly 14 and body 16. The housing 210 is formed to include an annular channel 232 for receipt of an attachment flange 242 of the thumb screw 212 to facilitate rotational movement of the thumb screw 212 about its longitudinal axis 244 relative to the housing 210.

The thumb screw 212 includes a proximal wall 234, a distal wall 236, an outer wall 238, an inner wall 240, a proximal attachment flange 242 and a longitudinal axis 244. The attachment flange 242 extends from the proximal wall 234 and is configured to cooperate with the channel 232 in the housing 210 to mount the thumb screw 212 to the housing 210 in a manner facilitating rotation of the thumb 212 screw about its longitudinal axis 244, which coincides with the longitudinal axis 222 of the housing 210, relative to the housing 210. The inner wall 240 of the thumb screw 212 includes a thread 246 configured to cooperate with the external thread 42 adjacent the distal end of the hollow shaft 18 to control the longitudinal movement of the hollow shaft 18 relative to the thumb screw assembly 14 and the body 16 upon rotation of the thumb screw 212. The outer wall 238 of the thumb screw 212 may be knurled to facilitate rotation of the thumb screw.

The removable drill guide assembly 32 includes an attachment device 250, a drill guide sleeve 252 and a drill guide 254. The attachment device 250 includes clamp 256, a drill guide arm 258 and a ball end 260. In the illustrated attachment device, the clamp 256 includes a semi-cylindrical curved plate 262 having a width 264 and a radius of curvature 266 sized to be received in the guide-receiving channel 64 of the body 16. A set screw 268 extends through a threaded hole 270 adjacent one end of the curved plate 262 which, upon tightening, secures the clamp 256 to the body 16. Clamp 256 permits the removable drill guide assembly 32 to be secured in substantially any desired radial position relative to the body 16. Loosening of the set screw 268 permits the clamp 256 to be rotated within the channel 64 about the longitudinal axis 66 of the body 16 or to be removed from the body 16 when so desired.

In the illustrated attachment device 250 the drill guide arm 258 extends radially outwardly and downwardly from a central portion 272 of the convex surface 274 of the curved plate 262. The drill guide arm 258 includes a first straight portion 276 adjacent a first end 278 and a second straight portion 280 extending at an angle 282 relative to the first straight portion 276 adjacent a second end 284. The drill guide arm 258 is attached at the first end 278 to the curved plate 262 of the clamp 256 and is attached at the second end 284 to the ball end 260. The ball end 260 has a diameter sized to be received in a reticulation cavity 288 of a socket 290 of the drill guide sleeve 252.

The drill guide sleeve 252 includes the socket 290 and a housing. In the illustrated embodiment, the housing includes an outside wall, a distal end wall, a proximal end wall an inside guide cavity wall and a longitudinal axis. The outside wall and inside guide cavity wall are formed generally concentrically about the longitudinal axis. The inside guide cavity wall defines a guide cavity extending between a proximal opening in the proximal end wall and a distal opening in the distal end wall. The guide cavity has an inside diameter sized to permit the drill guide 254 to be received therein.

The socket 290 is attached to the outside wall of the housing. The socket 290 includes an outer wall, an end wall, a cylindrical cavity wall and a circular bottom wall that define the reticulation cavity 288. The cylindrical cavity wall extends from an opening formed in the end wall to the circular bottom wall. The opening and reticulation cavity 288 both have a diameter slightly greater than but approximately equal to the diameter of the ball end 260. In the illustrated embodiment, the reticulation cavity 288 has a depth greater than the radius, i.e. half the diameter of the ball end 260. Thus the ball end 260 can be inserted through the opening and be received at least partially within the reticulation cavity 288 to couple the guide sleeve 252 to the attachment 250. When the end ball 260 is received in the reticulation cavity 288, the guide sleeve 252 can be positioned in the desired orientation to facilitate guided drilling through a plate into the bone to be repaired in the desired location. An orientation locking screw can be tightened to lock the guide sleeve 252 in the desired orientation.

A threaded screw hole extends through the socket 290 between the outer wall and the cylindrical cavity wall. The threaded screw hole is sized and threaded to receive the threaded shaft of the orientation locking set screw therethrough. The orientation locking screw includes a head coupled to one end of the threaded shaft. The head that may be knurled on its outer wall to facilitate turning the orientation locking screw. When turning the orientation locking screw in a first direction, the free end of the shaft is urged into frictional engagement with the outer surface of the end ball 260 and urges the opposite side of the end ball 260 into frictional engagement with the cylindrical side wall of the reticulation cavity 288. This frictional engagement between the end ball 260 and the free end of the orientation locking screw and the cylindrical cavity wall of the reticulation cavity 288 locks the guide sleeve 252 in the desired orientation. Turning the locking screw in the opposite direction urges the free end of the shaft of the locking screw away from the outer surface of the end ball 260 allowing the guide sleeve 252 to be reoriented if desired. Alternatively, the guide sleeve 252 can be decoupled from the attachment device 250.

Drill guide 254 includes a top flange, a grip, a housing, an orientation pin, a cylindrical guide wall and a longitudinal axis. The housing is formed to include a first end, a second end wall, and an outer cylindrical wall. The outer cylindrical wall has an outside diameter slightly less than but approximately equal to the inside diameter of the cavity in the guide sleeve 252. The flange includes a top wall, a bottom wall and an outer cylindrical wall. The outer cylindrical wall has an outside diameter greater than the inside diameter of the cavity in the guide sleeve 252. Thus, the drill guide 254 is configured to have the housing be received in the cavity of the sleeve guide 252 with the bottom wall of the flange resting on the proximal end wall of the housing of the sleeve guide 252.

The grip extends outwardly and downwardly from the outer wall of the flange. The grip is provided to facilitate single handed manipulation of the device 10.

In the assembled device 10, the plate fixation pin 12 is received in the lumen 38 of the hollow shaft 18, the hollow shaft 18 is received through the cavity 224 of the thumb screw assembly 14 and the shaft-receiving bore 58 of the body 16, the desired hook assembly 22 is coupled to the attachment flange 54 of the body 16 and positioned below (proximally) the bone-engaging assembly 24 which is attached to the proximal end of the hollow shaft 18. In the fully assembled device 10, the removable drill guide assembly 32 is coupled to the body 16.

In use the thumb screw 14 is utilized to control the longitudinal movement of the hollow shaft 18 relative to the body 16 and the hook assembly 22 to urge the bone-engaging assembly 24 toward and away from the hook assembly 22. The two feet 114, 116 of the bone-engaging assembly 24 extend proximally beyond the proximal end of the hollow shaft 18. The feet 114, 116 are constrained to move in the vertical direction only. The feet 114, 116 in conjunction with the bone-engaging arm 156 of the hook assembly 22 facilitate reduction of a fracture in a bone received therebetween. As previously mentioned, a plurality of hook assemblies 22 may be provided having differing dimensions and configurations to permit the surgeon to select the optimal hook assembly 22 for the bone on which the reduction procedure is being performed. Each of the plurality of hook assemblies 22 includes an attachment housing 150 configured to receive the attachment flange 54 therein for mounting the hook assembly 22 to the body 16.

The plate fixation pin 12 has its shaft 194 received in the lumen 38 in the hollow shaft 18 and its external thread 206 in engagement with the internal thread 44 adjacent the distal end of the lumen 38 of the hollow shaft 18. The external thread 206 and internal thread 44 cooperate to control longitudinal movement of the plate fixation pin 12 relative to the hollow shaft 18. Initially, upon engagement of the external thread 206 and the internal thread 44, the proximal end of the shaft 194 of the plate fixation pin 12, the plate-engaging end 202 is disposed adjacent the proximal end of the shaft 18. In this position the plate-engaging end 202 is displaced distally from the bone-engaging ends 146, 148 of the feet 114, 116. The plate fixation pin 12 moves longitudinally with respect to the shaft 18 as a result of rotation of the pin 12. Upon cessation of rotation of the pin 12, the external thread 206 and internal thread 44 cooperate to fix the position of the plate fixation pin 12 relative to the hollow shaft 18. Thus, the plate fixation pin 12 can be locked in any desired position relative to the shaft 18.

The handle 20 facilitates single handed operation of the device 10. While not illustrated, it is within the scope of the disclosure to couple the handle 20 to the body 16 in a manner that facilitates rotation of the handle 20 about the longitudinal axis 66 of the body 16 through 360 degrees. Once positioned in the desired position, the handle 20 may be locked in that position relative to the body 16 to reduce interference with the surgical procedure.

As previously mentioned the modular removable drill guide assembly 32 may be coupled to or decoupled from the medial portion 28 of the device 10. Illustratively, the drill guide assembly 32 is coupled in the channel 64 below the attachment location of the handle 20.

A plurality of drill guides 254, each configured to have their housings be received in the cavity of the drill guide sleeve 252 may be provided within the scope of the disclosure. The plurality of drill guides 254 may include differently sized cylindrical guide walls to facilitate different sizes of drills and different overall lengths. The surgeon can thus select the optimal drill guide 254 from the plurality of drill guides 254 for the operation being performed. The drill guide 254 can be changed to accommodate various sizes of screws and plates 400 to be used in the surgical procedure.

As mentioned above the removable drill guide assembly 32 can be placed in any radial position relative to the device 10 and the guide sleeve 252 and drill guide 254 received therein can be oriented in the desired position for optimal guided drilling results.

This device 10 is intended to be placed around fractures of the bones of the hands or feet. The handle 20 may be utilized to position the device 10 around a fractured region of bone 402 using a single hand operation procedure. The handle 20 is utilized to guide the device 10 relative to the fractured bone 400 so that the bone 400 is placed between the feet 114, 116 of the bone-engaging assembly 24 and the hook assembly 22. Once positioned around the fractured bone 400, the thumb screw of the thumb screw assembly 14 is turned causing the hollow shaft 18 and the bone-engaging assembly 24 attached thereto to move longitudinally relative to the body 16 toward the hook assembly 22. Since the attachment flange 54 and attachment housing 150 are captured between the frame members 110, 112 of the bone-engaging assembly 24 and the bone-engaging assembly 24 is rigidly affixed to the hollow shaft 18, the hollow shaft 18 and bone-engaging assembly 24 are constrained to move longitudinally without rotating.

The thumbscrew 14 is rotated in the appropriate direction until both the hook assembly 22 and the bone-engaging ends 146, 148 of the feet 114, 116 of the bone-engaging assembly 24 strike the bone and cooperate to reduce the fracture. Since the hollow shaft 18 and bone-engaging assembly 24 are constrained against rotational movement, the feet 114, 116 cannot rotate during the longitudinal movement and thus cannot misalign the fracture. As mentioned above, the surgeon can select from a plurality of differently sized and configured hook assemblies 22 so that the optimal hook assembly 22 is attached to the attachment flange 54 for the size of bone and procedure being performed.

Figure 1:
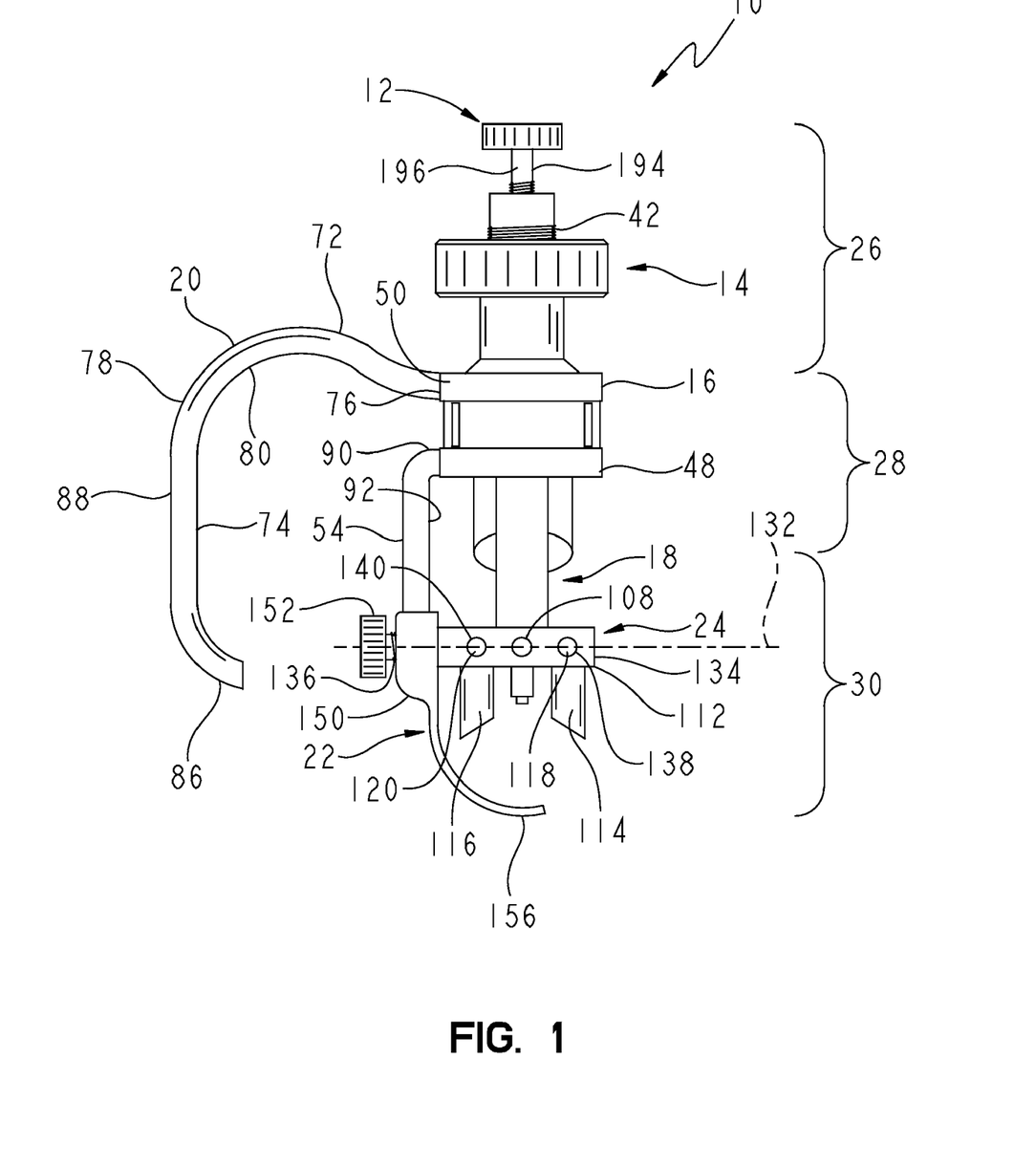
FIG. 1 is a perspective view of a disclosed device for facilitating reduction and repair of fractures of small bones.
Figure 2:
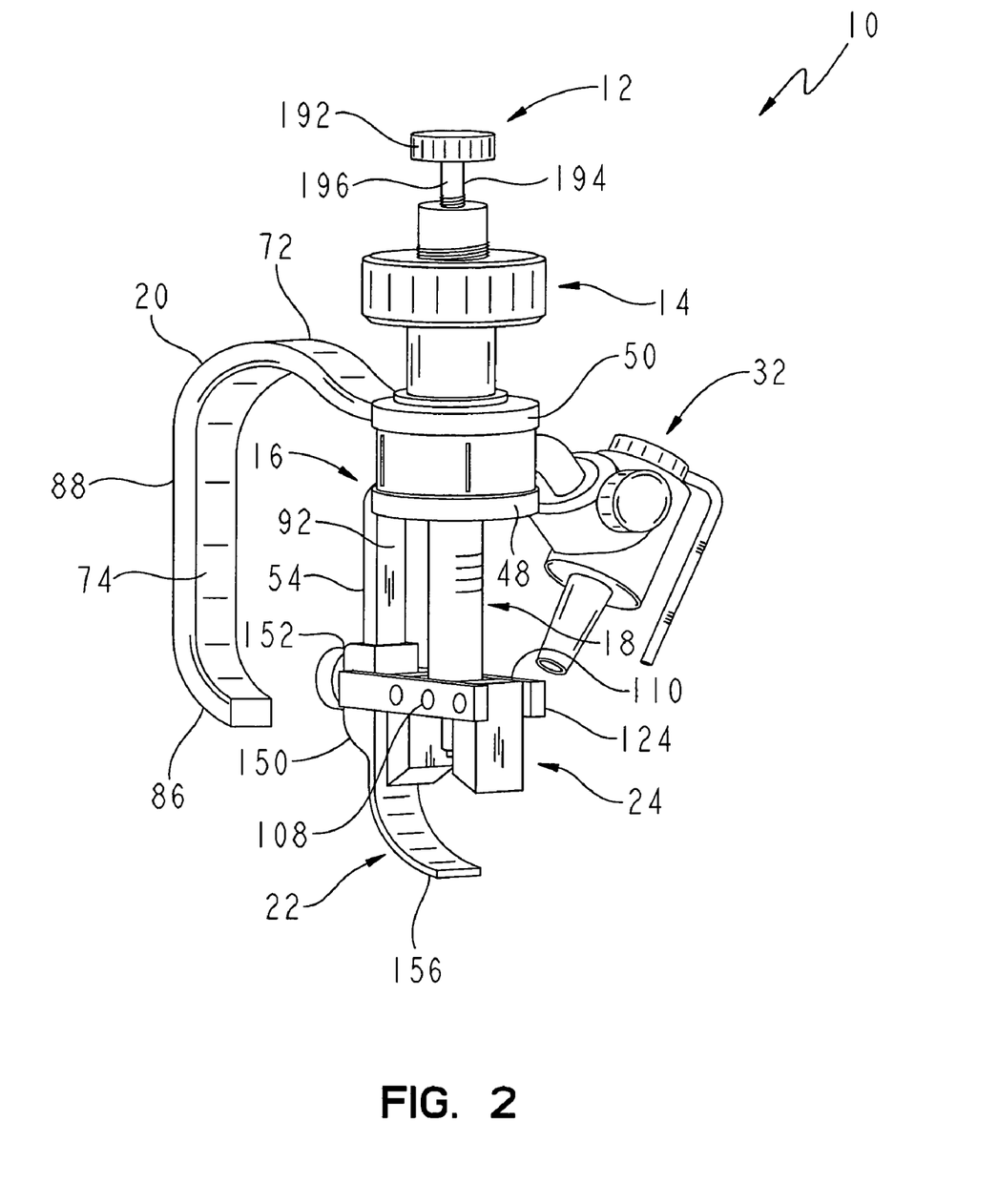
FIG. 2 is another perspective view of the device for facilitating reduction and repair of fractures of small bones of FIG. 1.
Figure 3:
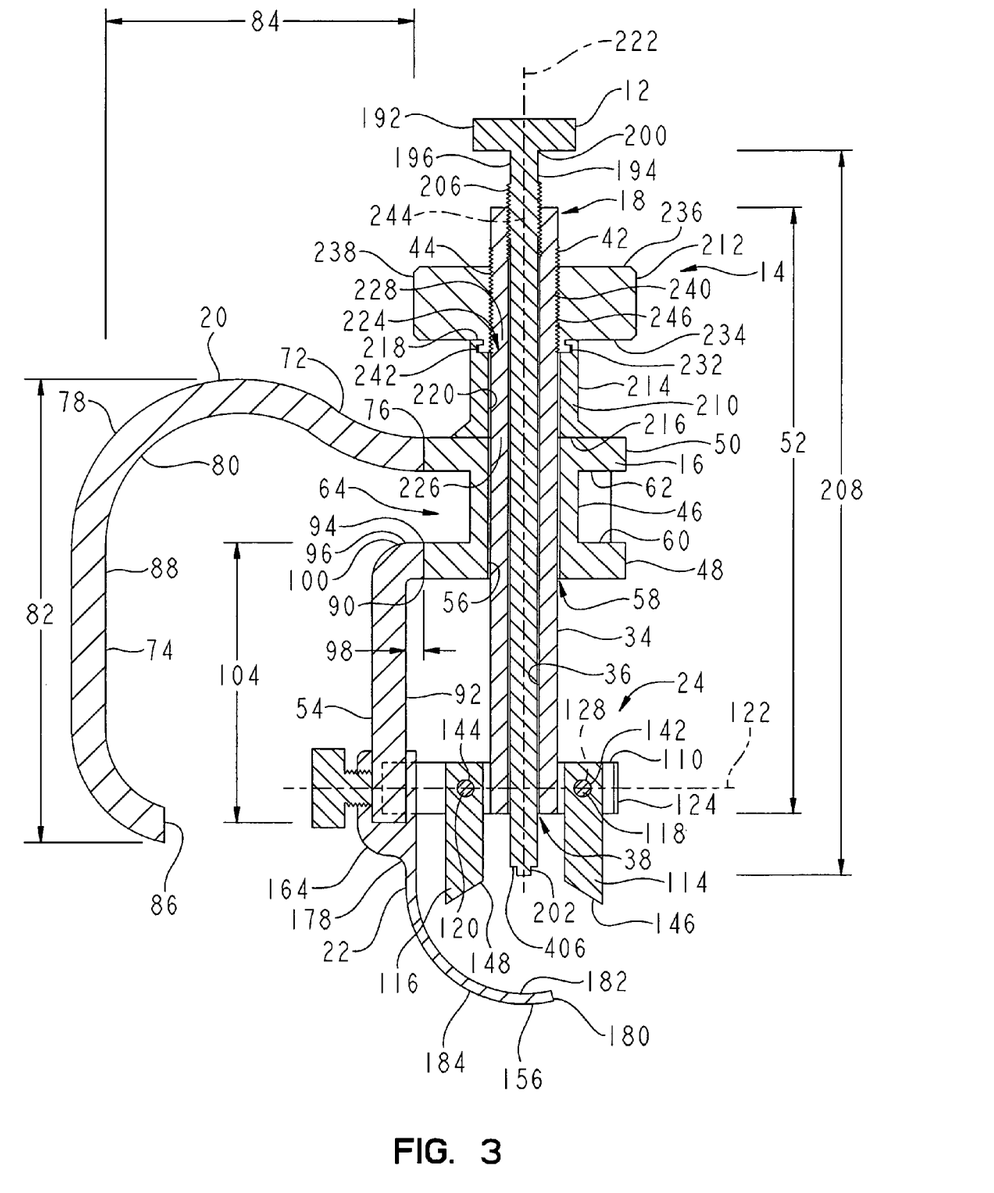
FIG. 3 is a sectional view of the device for facilitating reduction and repair of fractures of small bones of FIG. 1.
Figure 3A:
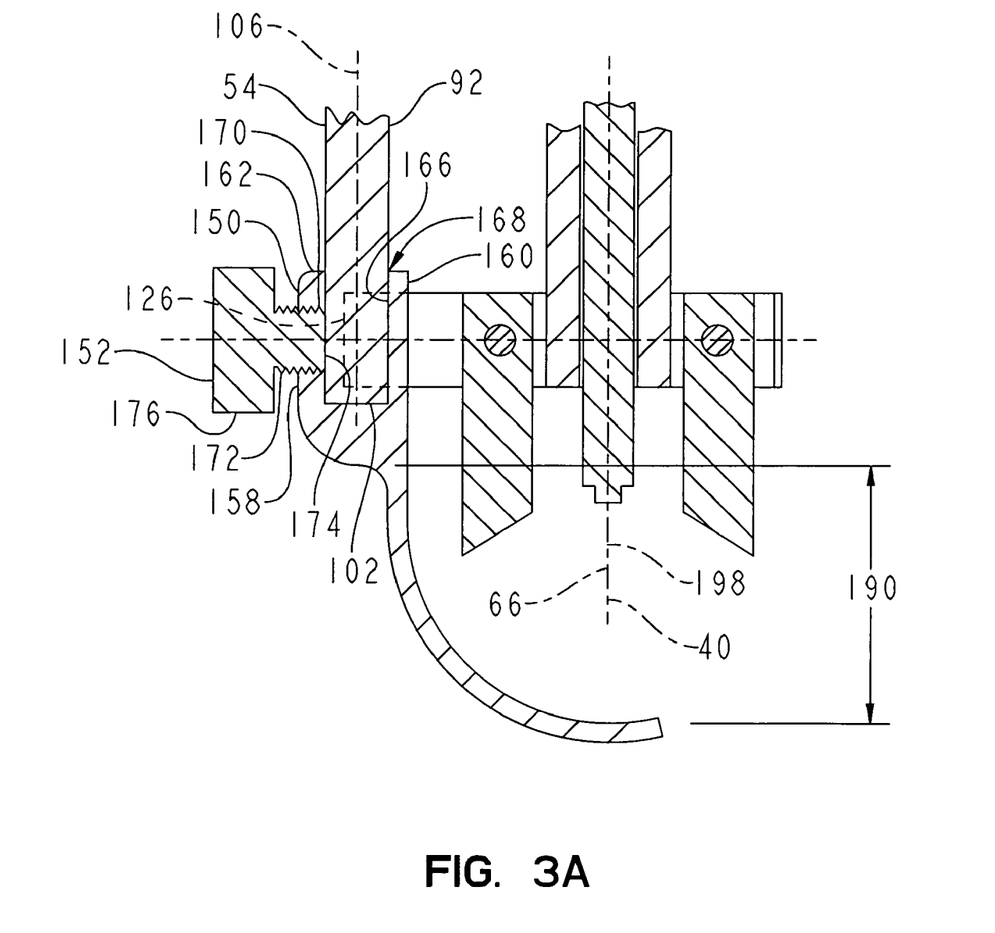
FIG. 3A is an enlarged sectional view of the proximal section of the device for facilitating reduction and repair of fractures of small bones of FIG. 1 (and FIG. 3)
Figure 4:
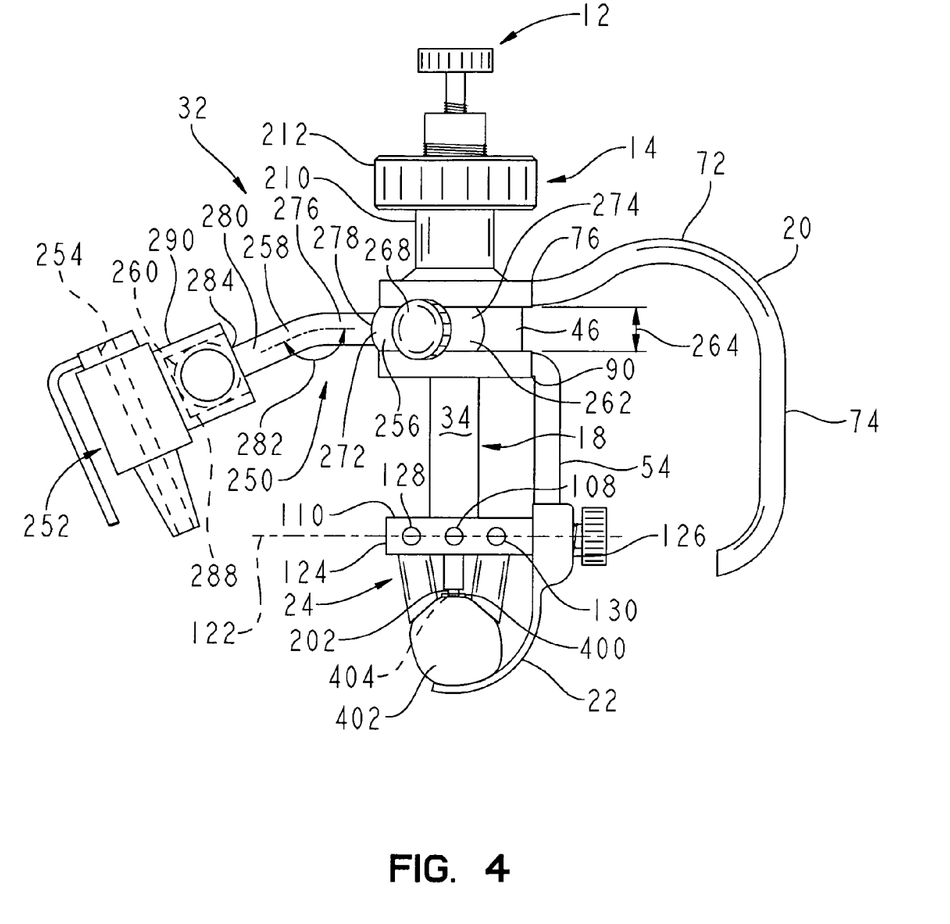
FIG. 4 is a view of the device for facilitating reduction and repair of fractures of small bones of FIG. 1 showing a bone captured between the hook arm and bone-engaging assembly and a plate temporarily affixed to the bone by the plate fixation pin.

Once the hook assembly 22 and the feet 114, 116 of the bone-engaging assembly 24 have cooperated to reduce the fracture, as shown, for example, in FIG. 4, the plate fixation pin 12 is utilized to provide temporary plate 400 to bone 402 fixation. The plate fixation pin 12 is moved longitudinally relative to the hollow shaft 18 so that the free end 202 of the shaft 194 of the plate fixation pin 12 is displaced sufficiently from the bone 402 to allow a plate 400 with a fixation hole 404 formed therein to be slid on the bone 402 between the feet 114, 116 of the bone engaging assembly 24. The fixation pin 12 is then moved longitudinally in the proximal direction relative to the hollow shaft 18 until the pin-shaped free end 202 of the plate fixation pin 12 passes through the fixation hole 404 of the plate 400 and into contact with the bone 402. The length of the pin shaped free end 202 is such that when the free end of the fixation pin 12 contacts the bone 400, the ring wall 406 formed between the shaft 194 and the free end 202 of the fixation pin 12 engages the distal surface of the plate 400. Once in contact with the bone 402, the external threads 206 adjacent the distal end of the shaft 194 of the plate fixation pin 12 and the internal threads 44 adjacent the distal end of the lumen 38 of the hollow tube 18 cooperate to lock the plate fixation pin 12 in the desired location temporarily affixing the plate 400 to the bone 402.

Since the disclosed handle 20 is able to spin 360 degrees about the longitudinal axis 66 of the body 16, the handle 20 can then be positioned so that it does not interfere with the remainder of the procedure. If the removable drill guide assembly 32 has not been previously affixed to the body 16, the semi-cylindrical plate 262 of the clamp 256 is received in the channel 64 of the body 16 and clamped in a desired radial location by tightening the set screw 268 to secure the drill guide arm 258 to the body 16. A plurality of drill guide arms 258 configured as described above but having arms of differing length may be provided so that the surgeon can select the optimal drill guide arm 258 for the procedure being performed and the length of the plate 400 required for such procedure.

Once the optimal drill guide arm 258 is selected and attached to the body 16 of the device 10, the drill guide sleeve 252 is attached to the drill guide arm 258 by capturing the ball end 260 of the drill guide arm 258 in the reticulation cavity 288 of the socket 290 of the drill guide sleeve 252. With the ball end 260 received in the reticulation cavity 288, the drill guide sleeve 252 may be oriented in an anticipated desired orientation for the screw hole to be drilled. The drill guide sleeve 252 may then be locked in the anticipated desired orientation by tightening the orientation screw until the ball end 260 is brought into frictional engagement with the free end of the screw and the inside cavity wall radially opposite the screw hole extending through the socket 290. The housing of the desired drill guide 254 for the size of drill to be used in the procedure is inserted into the drill guide cavity in the drill guide sleeve 252 until bottom wall of the flange engages the distal wall of the sleeve 252.

The orientation pin of the drill guide 254 provides a visual cue for the alignment of the hole to be drilled. After insertion of the drill guide 254 into the drill guide sleeve 252, the surgeon may loosen the set screw and reorient the drill guide sleeve 252 if the orientation pin indicates that the anticipated desired orientation was incorrect. When the drill guide 254 received in the drill guide sleeve 252 is oriented in the desired position, the set screw is tightened to lock the drill guide 254 and sleeve 252 in the desired orientation.

The appropriately sized drill for the procedure and for the selected drill guide 254 is then inserted through the cavity defined by the cylindrical guide wall of the drill guide 254 and utilized to drill attachment holes through the plate 400 and the bone 402. Fasteners (not shown) are then inserted through the drilled attachment holes through the plate 400 and into the bone 402 to secure the plate 400 to the bone 402. Bone screws are typically used as fasteners with the bone screws being screwed into the attachment holes to secure the plate 400 to the fractured bone 402. The drill guide 254 may then be repositioned and oriented to drill any additional attachment holes required by the procedure being performed. Once the desired number of screws or other fasteners is inserted through the drilled attachment holes, the thumb screw 14 is rotated in the opposite direction to move the free end 202 and ring wall 406 of the plate fixation pin 12 out of engagement with the bone 402 and plate 400, respectively, and to disengage the hook assembly 22 and the bone-engaging assembly 24 from the bone 402.

The disclosed device advantageously allows a surgeon to perform multiple tasks utilizing a single instrument 10. The surgeon is able to reduce the fracture in the bone 402 utilizing the disclosed instrument 10. The surgeon is also able to temporarily affix a bone plate 400 in a desired position to the bone 402 containing the reduced fracture. While the plate 400 is affixed to the bone 402, appropriate attachment holes may be drilled through the plate 400 into the reduced bone 402 so that bone screws or other fasteners can be utilized to more permanently affix the plate 400 to the bone 402. Utilizing the disclosed removable drill guide assembly 32, these attachment holes can be drilled in a guided manner. The disclosed instrument 10 saves the surgeon time in performing the repair of the fracture by reducing the number of clamps that must be used. Also the accuracy of the drilling of the attachment holes is increased when the removable drill guide assembly 32 is utilized. The orientation guide 346 on the drill guide 254 provides a visual reference for the location and orientation of the attachment hole to be drilled.

Although specific embodiments of the invention have been described herein, other embodiments may be perceived by those skilled in the art without departing from the scope of the invention as defined by the following claims. For example, although the invention has been described in terms of reduction and repair of fractures in the bones of the hand and foot, but may be utilized in reduction and repair of other bones, particularly other small bones such as ribs and bones in young patients. Additionally, it is noted that to facilitate avoidance of various tendons or other soft tissues in alternative embodiments the arm of the hook assembly 22 may be replaced with an arm of greater or lesser curvature or another geometry differing from the exemplary embodiment, may be laterally wider or thinner than the exemplary embodiment, may be replaced with a plurality of forklift-like spaced apart arms, or may be implemented in any other suitable alternative configuration. The lateral spacing between forklift-like arms may be adjustable. Further, in alternative embodiments the first foot 114 and the second foot 116 may be individually vertically adjustable and the drill guide assembly 32 may be replaced with any of a number of suitable alternative guide assemblies for aligning different drills, bone saws, or other surgical tools.

What is claimed is:

1. A surgical instrument comprising:
a body portion;
a first bone-engaging member coupled to said body portion and defining a first bone contact surface;
a second bone-engaging member movably coupled to said body portion and defining a second bone contact surface, said second bone-engaging member being movable in relation to said body portion along an axis so as to cause said second bone-engaging member to be moved in relation to said first bone-engaging member, wherein the first bone contact surface and the second bone contact surface define a first space therebetween configured to receive a bone;
a plate fixation member movably coupled to said body portion and defining plate contact surface, said plate fixation member being movable in relation to said body portion so as to cause said plate fixation member to be moved in relation to said first bone-engaging member, wherein the plate contact surface and the first bone contact surface define a second space therebetween configured to receive the bone and a bone plate; and
a thumb wheel,
wherein said body portion includes a hollow shaft and said thumb wheel is movably coupled to said hollow shaft to control movement of said hollow shaft relative to at least one of said first bone-engaging member and said second bone engaging member,
wherein said hollow shaft defines said axis,
wherein said plate fixation member includes a longitudinal pin movably coupled to said body portion, and said longitudinal pin is aligned with said axis,
wherein said longitudinal pin extends through said hollow shaft,
wherein said first bone-engaging member includes a hooked arm, and
wherein said hooked arm is positioned to intersect said axis.

2. A surgical system comprising:
a first bone engaging component;
a second bone engaging component aligned along an axis with the first bone engaging component and movable with respect to the first bone engaging component along the axis in a direction toward the first bone engaging component, the second bone engaging component operably connected to the first bone engaging component for securing a bone therebetween; and a plate fixation component movable with respect to the first bone engaging component and the second bone engaging component along the axis in a direction toward the second bone engaging component, the plate fixation component operably connected to the second bone engaging component for securing a bone therebetween, wherein the first bone engaging component includes a first bone contacting surface and a second bone contacting surface;

wherein the plate fixation component is located between the first bone contacting surface and the second bone contacting surface, and wherein the second bone engaging component comprises an arm extending substantially perpendicular to the axis at a location beneath the first bone contacting surface and a second bone contacting surface.

3. The system of claim 2, wherein each of the first bone contacting surface and the second bone contacting surface are positioned at an acute angle with the axis.

4. The system of claim 2, wherein the plate fixation component comprises an end portion configured to fit within an opening of a bone plate.

5. A surgical system comprising:

a first bone engaging component;

a second bone engaging component aligned along an axis with the first bone engaging component and movable with respect to the first bone engaging component along the axis in a direction toward the first bone engaging component, the second bone engaging component operably connected to the first bone engaging component for securing a bone therebetween;

a plate fixation component movable with respect to the first bone engaging component and the second bone engaging component along the axis in a direction toward the second bone engaging component, the plate fixation component operably connected to the second bone engaging component for securing a bone therebetween; and a body configured to (i) removably support the second bone engaging component, (ii) rotatably support the first bone engaging component, and (iii) rotatably support the plate fixation component, wherein the second bone engaging component is one of a plurality of second bone engaging components, each of the plurality of second bone engaging components having a dimension different from the dimension of the other of the plurality of second bone engaging components.

* * * * *

UNITED STATES PATENT AND TRADEMARK OFFICE
CERTIFICATE OF CORRECTION

| | | |
|---|---|---|
| PATENT NO. | : 7,850,696 B2 | Page 1 of 1 |
| APPLICATION NO. | : 11/237009 | |
| DATED | : December 14, 2010 | |
| INVENTOR(S) | : Mark H. Gonzalez et al. | |

It is certified that error appears in the above-identified patent and that said Letters Patent is hereby corrected as shown below:

<u>Column 5,</u>
Line 49, after "attachment housing 150" delete "is"

<u>Column 7,</u>
Line 22, replace "thumb 212 screw" with --thumb screw 212--

<u>Column 7,</u>
Line 62, after "a proximal end wall" insert --,--

Signed and Sealed this
Nineteenth Day of February, 2013

Teresa Stanek Rea
*Acting Director of the United States Patent and Trademark Office*